US00RE48861E

(19) United States
(12) Reissued Patent
Rongione et al.

(10) Patent Number: US RE48,861 E
(45) Date of Reissued Patent: Dec. 28, 2021

(54) ELIMINATION OF ORGANOHALO AND OXIRANE SPECIES IN CARBOXYLIC ACID ESTER STREAMS

(71) Applicant: STEPAN SPECIALTY PRODUCTS, LLC, Maywood, NJ (US)

(72) Inventors: Joseph C. Rongione, Middletown, NJ (US); Jenifer Heydinger-Galante, Oakland, NJ (US)

(73) Assignee: STEPAN SPECIALTY PRODUCTS, LLC, Maywood, NJ (US)

(21) Appl. No.: 16/825,542

(22) Filed: Mar. 20, 2020

Related U.S. Patent Documents

Reissue of:
(64) Patent No.: 9,051,260
Issued: Jun. 9, 2015
Appl. No.: 13/816,998
PCT Filed: Sep. 2, 2011
PCT No.: PCT/US2011/050289
§ 371 (c)(1),
(2) Date: Apr. 15, 2013
PCT Pub. No.: WO2012/031176
PCT Pub. Date: Mar. 8, 2012

U.S. Applications:
(60) Provisional application No. 61/380,013, filed on Sep. 3, 2010.

(51) Int. Cl.

| | |
|---|---|
| ***C07C 67/48*** | (2006.01) |
| ***C07C 51/41*** | (2006.01) |
| ***C07C 51/487*** | (2006.01) |
| ***C11B 3/00*** | (2006.01) |
| ***C11B 3/06*** | (2006.01) |
| ***C11B 7/00*** | (2006.01) |
| ***C11C 1/08*** | (2006.01) |

(52) U.S. Cl.
CPC ..... *C07C 67/48* (2013.01); *C07C 51/412* (2013.01); *C07C 51/487* (2013.01); *C11B 3/001* (2013.01); *C11B 3/06* (2013.01); *C11B 7/0083* (2013.01); *C11C 1/08* (2013.01)

(58) Field of Classification Search
CPC ..... C07C 67/48; C07C 51/487; C07C 51/412; C11B 3/001; C11B 7/0083; C11B 3/06; C11C 1/08
See application file for complete search history.

(56) References Cited

U.S. PATENT DOCUMENTS

| | | | | |
|---|---|---|---|---|
| 1,885,281 | A | 11/1932 | Newton | |
| 2,197,339 | A | 4/1940 | Gooding | |
| 3,413,324 | A | 11/1968 | Seip | |
| 4,025,540 | A * | 5/1977 | Kleemann et al. | 554/149 |
| 4,157,405 | A | 6/1979 | Yasuda | |
| 4,280,962 | A | 7/1981 | Watanabe | |
| 5,315,021 | A | 5/1994 | Beharry | |
| 6,111,120 | A | 8/2000 | Myers | |
| 2003/0225295 | A1 | 12/2003 | Yan et al. | |
| 2009/0023808 | A1 * | 1/2009 | Raman et al. | 514/549 |

FOREIGN PATENT DOCUMENTS

| | | | |
|---|---|---|---|
| CN | 102334563 | A | 2/2012 |
| DE | 102010007138 | A1 | 8/2011 |
| EP | 0361595 | A1 | 4/1990 |
| EP | 3361595 | A1 | 4/1990 |
| EP | 2471897 | A1 | 7/2012 |
| EP | 2548942 | A1 | 1/2013 |
| EP | 2594625 | A1 | 5/2013 |
| FR | 2779447 | A1 * | 12/1999 |
| FR | 2779447 | | 12/2003 |
| GB | 764833 | A | 1/1957 |
| JP | 2011-195622 | A | 11/2011 |
| WO | 2005-021476 | A1 | 3/2005 |
| WO | WO 2005/021476 | | 3/2005 |
| WO | 2009/115248 | A1 | 9/2009 |
| WO | 2010/080019 | A2 | 7/2010 |
| WO | 2010126136 | A1 | 11/2010 |
| WO | 2011-002275 | A1 | 1/2011 |
| WO | WO 2011/002275 | | 1/2011 |
| WO | 2011/055732 | A1 | 5/2011 |
| WO | 2012/031176 | A1 | 3/2012 |
| WO | 2010/126136 | A1 | 11/2012 |
| WO | 2011/040539 | A1 | 2/2013 |

OTHER PUBLICATIONS

PCT Request in International application No. PCT/US11/50289, Sep. 2, 2011 (4 pages).
Certified U.S. Appl. No. 61/380,013, filed Sep. 3, 2010 (29 pages).
Inter-Company Agreement entered into as of Feb. 1, 2013, between Stepan Company and Stepan Specialty Products, LLC, and cover letter (19 pages).
LinkedIn profile of Jenifer Galante, https://www.linkedin.com/in/jenifer-galante-8041184/; retrieved from the internet on Jul. 17, 2018 (2 pages).
Rüdiger Weiβhaar, Determination of total 3-chloropropane-1,2-diol (3-MCPD) in edible oils by cleavage of MCPD esters with sodium methoxide, Eur. J. Lipid Sci. Technol. 2008, 110, 183-186 (4 pages).
European Search Opinion, European Application No. 11 882 699.2 (2 pages).
Bertrand Matthäus, What are the Possibilities to Reduce the Content of 3-MCPD Esters in Edible Oils?, Max Rubner-Institute, Federal Research Institute for Nutrition and Food; Department for Lipid Research Piusallee 68/76; 48147 Münster, Germany, presentation dated May 25, 2010 (26 pages).
Dr. Ines Baer, Chloropropanols and Their Esters, IRMM, Institute for Reference Materials, and Measurements, Geel, Belgium, http://irmm.jrc.ec.europa.eu/, Joint Research Center—European Commission, IV Food Contaminants Seminar, presentation dated Sep. 20, 2010 (35 pages).

(Continued)

*Primary Examiner* — Jerry D Johnson
(74) *Attorney, Agent, or Firm* — McAndrews, Held & Malloy, Ltd.

(57) ABSTRACT

The present technology provides a process of reducing, removing or eliminating organohalo, glycidol, and oxirane species from carboxylic acid esters streams and crude and refined triglyceride oils to provide a carboxylic acid ester stream or triglyceride oil with reduced levels or essentially free of organohalo, glycidyl or other oxirane species. The process includes adding to the carboxylic acid ester stream or triglyceride oil an amount of a carboxylate anion and a cation counterion sufficient to react with the organohalo, glycidyl and oxirane species present.

36 Claims, No Drawings

(56) References Cited

OTHER PUBLICATIONS

Jan Smidrkal et al., Formation of Acylglycerol Chloro Derivatives in Vegetable Oils and Mitigation Strategy, Czech J. Food Sci., vol. 29, 2011, No. 4:449-456 (9 pages).
Jan Velisek et al., 3-Chloropropane-1,2-diol in Models Simulating Processed Foods: Precursors and Agents Causing its Decomposition, Czech J. Food Sci, 2003, vol. 21, No. 5:153-161 (9 pages).
Gerrit van Duijn, Potential ways of reduction of 3-MCPD esters in vegetable oils, ILSI Conference, presentation dated Feb. 5-6, 2009 (15 pages).
Inform magazine, Apr. 2009, pp. 1-3 (3 pages).
Inform magazine, Apr. 2009, pp. 1-3, in color (3 pages).
K. Franke et al., Influence of chemical refining process and oil type on bound 3-chloro-1,2-propanediol contents in palm oil and rapeseed oil, LWT—Food Science Technology 42 (2009) 1751-1754 (4 pages).
M. Rossi et al., The role of bleaching clays and synthetic silica in palm oil physical refining, Food Chemistry 82 (2003) 291-296, www.elsevier.com/locate/foodchem (6 pages).
Prof. Madya Dr. Noor Azian Morad, et al., Process Design in Degumming and Bleaching of Palm Oil, Research Vote No. 74198, Centre of Lipids Engineering and Applied Research (Clear) Universiti Teknologi Malaysia, p. 22, Nov. 2006 (2 pages).
F. Pudel et al., On the necessity of edible oil refining and possible sources of 3-MCPD and glycidyl esters, Eur. J. Lipid Sci. Technol. 2011, 113, 368-373 (6 pages).
F. Pudel et al., On the necessity of edible oil refining and possible sources of 3-MCPD and glycidel esters, Eur. J. Lipid Sci. Technol. 2011, 113, Issue 3, https://doi.org/10.1002/ejlt.201000460, first published Jan. 13, 2011, abstract (2 pages).
B. Matthäus et al., ILSI Workshop on MCPD and Glycidyl esters in Food Products, Nov. 9-10, 2012, Brussels, presentation dated Apr. 29-May 2, 2012 (26 pages).
F. Pudel et al., Mitigation of 3-MCPD and G Esters in refined palm oils, 103rd AOCS Annual Meeting & Expo, presentation dated Apr. 29-May 2, 2012, Long Beach, CA (25 pages).
BfR Opinion No. 047/2007, Infant formula and follow-up formula may contain harmful 3-MCPD fatty acid esters, Dec. 11, 2007 (6 pages).
W. Seefelder, Esters of 3-chloro-1,2-propanediol (3-MCPD) in vegetable oils: Significance in the formation of 3-MCPD, Food Additives and Contaminants, Apr. 2008; 25(4): 391-400 (10 pages).
W.S. Choo et al.. The optimization of conditions for the production of acid-hydrolysed winged bean and soybean proteins with reduction of 3-monochloropropane-1,2-diol (3-MCPD), International Journal of Food Science and Technology 2004, 39, 947-958 (12 pages).
C. Crews, Analytical approaches for MCPD esters and glycidyl esters in food and biological samples: a review and future perspectives; Food Additives & Contaminants: Part A, 2012, 1-35, iFirst (35 pages).
John Christian Larsen, 3-MCPD Esters in Food Products, Summary Report of a Workshop held in Feb. 2009, in Brussels, Belgrium, ILSI Europe Report Series, dated Oct. 2009, pp. 4-6. (7 pages).
Lawrence C. Mitchell, Journal of the American Oil Chemists' Society, vol. 49, 1972, pp. 281-282 (2 pages).
Email from Katerina Starkova to Tore Kilerich Johansen dated Feb. 19, 2018 re Publication date of two articles in Czech Journal of Food Science. (1 page).
Morris Mattikow, Developments in the Refining of Oils With Sodium Carbonate, The Journal of the American Oil Chemists' Society, Jun. 1948, pp. 200-203 (4 pages).
M.E. Furrow et al., Practical Access to Highly Enantioentriched C-3 Building Blocks via Hydrolytic Kinetic Resolution, J. Org. Chem., 1998, 63(20), 6776-6777, DOI:10.1021/jo981332d, and supporting information (14 pages).
Collin G. Hamlet et al., Formulation and occurrence of esters of 3-chloropropane-1,2-diol (3-CPD) in foods: What we know and what we assume, Eur. J. Lipid Sci. Technol. 2011, 113, 279-303 (25 pages).
Bertrand Matthäus, Strategies for the reduction of 3-MCPD esters and related compounds in vegetable oils, Eur. J. Lipid Sci. Technol. 2011, 113, 380-386 (7 pages).
Bertrand Matthäus, Potential ways of reduction of 3-MCPD esters in vegetable oils/data on mitigation, ILSI Europe, Feb. 4-5, 2009, Brussels, Belgium, presentation dated Feb. 2009 (28 pages).
European Patent Office, Reasons for the Decision of the Opposition Division in the Opposition Proceedings against EP 1 965 823, in Application No. 06 839 697. 7, dated Oct. 4, 2018. (33 pages).
European Patent Office, Reasons for the Decision of the Opposition Division in the Opposition Proceedings against EP 2 429 574, in Application No. 10 774 475.7, dated Jan. 2, 2018 (31 pages).
European Patent Office, Preliminary opinion of the Opposition Division in the Opposition Proceedings against EP 2 940 044 in Application No. 15 165 133.8, dated Jul. 13, 2018 (19 pages).
European Patent Office, Preliminary opinion of the Opposition Division in the Opposition Proceedings against EP 2 215 124 in Application No. 08 798 550.3, dated Dec. 13, 2017 (19 pages).
European Patent Office, Preliminary opinion of the Board of Appeal in the Appeal Proceedings in appeal T0239/16-3.3.01 in Application No. 05012711.7 dated Jun. 14, 2017 (27 pages).
Declaration by Janet Catlett, Stepan Company Vice President, Chief Human Resources Officer, dated Feb. 19, 2019, with attachment A (7 pages).
Jun Ma, Curriculum Vitae, Company IP Officer, Bunge Loders Croklaan B.V. (2 pages).
PCT, International Search Report in International Application No. PCT/US11/50289, dated Feb. 10, 2012 (2 pages).
PCT, International Preliminary Report on Patentability in International Application No. PCT/US11/050289, dated Mar. 5, 2013 (9 pages).
European Patent Office, Supplementary European Patent Report, in Application No. EP 11 82 2699, dated May 26, 2014 (2 pages).
European Patent Office, European Search Opinion in Application No. 11 82 699.2 dated Jun. 11, 2014. (2 pages).
Patent Owner Stepan Reply to Notice of Opposition, in Opposition Proceedings of EP Patent No. 2 611 767, dated Feb. 22, 2019 (46 pages).
European Patent Office, Reply by EPO opposition division, in Application No. 11 822 699.2, dated Jun. 18, 2019 (11 pages).
Potters Clarkson letter to The European Patent Office in reply to Summons for Oral Proceedings with further submissions Nov. 11, 2019. (10 pages).
Cargill, Incorporated letter in reply to Summons for Oral Proceedings with further argumentation, Dec. 17, 2019. (14 pages).
Lederer & Keller letter to The European Patent Office in reply to Summons for Oral Proceedings with further submissions Jan. 2, 2020. (14 pages).
ZSP to The European Patent Office in reply to Summons to attend Oral Proceedings with further submissions Jan. 3, 2020. (20 pages).
Mathys & Squire to The European Patent Office in reply to Summons for Oral Proceedings with further submissions Jan. 3, 2020. (8 pages).
ZSP Grounds of Appeal to the European Patent Office, dated Nov. 6, 2020 (64 pages).
Cargill, Incorporated Reply to Appeal, dated Feb. 8, 2021 (49 pages).
Lederer & Keller Reply to Appeal, dated Mar. 17, 2021 (27 pages).
Bunge Loders Croklaan B.V. Reply to Appeal, dated Mar. 18, 2021 (66 pages).
D62 AAK AB Experimental Report, dated Mar. 18, 2021 (1 page).
AAK AB Reply to Appeal, dated Mar. 22, 2021 (39 pages).
Mitchell, Specific Diacid Triglycerides by a Simple Two-Step Procedure, J. Am. Oil Chem. Soc., 1972, 49, pp. 281-282 (2 pages).
Velisek et al., 3-Chloropropane-1,2-diol in Models Simulating Processed Foods: Precursors and Agents Causing its Decomposition, Czech J. Food Sci., 2003, vol. 21, No. 5, pp. 153-161 (9 pages).
Choo et al., The Optimization of Conditions for the Production of Acid-Hydrolysed Winged Bean and Soybean Proteins With Reduction of 3-monochloropropane-1,2-diol (3-MCPD), International Journal of Food Science and Technology, 2004, 39, pp. 947-958 (12 pages).

(56) References Cited

OTHER PUBLICATIONS

Franke et al., Influence of Chemical Refining Process and Oil Type on Bound 3-Chloro-1,2-Propanediol Contents in Palm Oil and Rapeseed Oil, LWT—Food Science and Technology, 2009, 42, 1751-1754 (4 pages).
Pudel et al., On the Necessity of Edible Oil Refining and Possible Sources of 3-MCPD and Glycidyl Esters, Eur. J. Lipid Sci. Technol., 2011, 113, pp. 368-373 (6 pages).
Smidrkal et al., Formation of Acylglycerol Chloro Derivatives in Vegetable Oils and Mitigation Strategy, Czech J. Food Sci., 2011, vol. 29, No. 4, pp. 449-456 (9 pages).
ZSP to The European Patent Office in reply to Opponent 1 dated Dec. 17, 2019, Opponent 3 dated Jan. 2, 2020 and Opponent 4 dated Jan. 3, 2020, dated Feb. 4, 2020. (27 pages).
European Patent Office, Decision in Application No. 11822699.2, dated Jun. 30, 2020 (30 pages).
AAK AB Opposition as filed, Jul. 25, 2018 (34 pages).
Bunge Loders Croklaan B.V. Opposition as filed, Jul. 26, 2018 (34 pages).
Cargill, Incorporated Opposition as filed, Jul. 19, 2018 (27 pages).
Lederer & Keller Patentanwalte Partnerschaft mbB Opposition as filed, Jul. 25, 2018 (27 pages).
Report of an experiment published in the opposition file (European Patent Register file EP 2611767) by Opposer Cargill, Incorporated on Jul. 19, 2018 (1 page).
Report of an experiment published in the opposition file (European Patent Register file EP 2611767) by Opposer AAK AB on Jul. 25, 2018 (2 pages).
Report of an experiment published in the opposition file (European Patent Register file EP 2611767) by Patent Owner Stepan Specialty Products LLC on Feb. 22, 2019 (1 page).
Report of an experiment published in the opposition file (European Patent Register file EP 2611767) by Opposer Bunge Loders Croklaan B.V. on Nov. 11, 2019 (1 page).
Report of an experiment published in the opposition file (European Patent Register file EP 2611767) by Opposer AAK AB on Jan. 3, 2020.
Search Report & Written Opinion issued in App. No. PCT/US2011/050289 (2012).
Baer, "Chloropropanols and their esters," *IV Food Contaminants Seminar*, retrieved from the internet on May 15, 2014: www.ital.sp.gov.br/ccqa/eventos/pos_evento/2010/iv-conali-01-e-02-de-setembro/chloropropanols_ines%20baer.pdf (Sep. 2, 2010).
Velisek et al., "3-Chloropropane-1,2-diol in Models Simulating Processed Foods: Precursors and Agents Causing Its Decomposition," *Czech J. Food Sci.*,'21(5): 153-161 (2003).

* cited by examiner

ELIMINATION OF ORGANOHALO AND OXIRANE SPECIES IN CARBOXYLIC ACID ESTER STREAMS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application a U.S. nationalization under 35 U.S.C. § 371 of International Application No. PCT/US2011/050289, filed Sep. 2, 2011, which claims priority to U.S. Provisional Application No. 61/380,013, filed on Sep. 3, 2010, with the title "Elimination of Oraganohalo and Oxirane Species in Carboxylic Acid Ester Streams," the contents of which are herein incorporated by reference in their entirety.

BACKGROUND OF THE INVENTION 3-chloro-1,2-propanediol (3-MCPD) is a well known organic chemical compound formed in foods. It is a byproduct of food processing, especially in heat processed, fat-containing foodstuff, where 3-MCPD is formed during the processing.

Recent studies have identified high levels of 3-MCPD esters in refined fats and oils, including edible oils. 3-chloro-1,2-propanediol (3-MCPDs) and their esters have been found in all refined vegetable oils. The processing and refining of oils leads to formation of these unwanted byproducts, organohalo species (for example, 3-chloro-1,2-propanediol (MCPDs)) and glycidol and their respective esters. Free MCPD has been found to exhibit genotoxic and carcinogenic effects in testing, and these effects have raised some concern, especially in the food industry. Glycidol is also a known genotoxic and carcinogenic compound. No toxicological profiles are known for the 3-MCPD esters or glycidyl esters. These esters' toxicities depend on their breakdown by lipases in the gut to the free 3-MCPD or glycerol species, which is a current area of concern and study.

Currently, there is limited and contradictory knowledge available about when and how 3-MPCD-esters are formed during the oil refining process. The highest 3-MPCD ester contents are found in refined oils whereas virgin or non-refined oils have lower content, sometimes below detection limits. There is some belief that heat pre-treatment of the seed (or fruit) may contribute to the levels in non-refined oils. Research into the mechanism of 3-MCPD/glycidol-ester formation is ongoing in the field.

BRIEF SUMMARY OF THE INVENTION

There is a need in the art to limit or eliminate the amounts of 3-MCPD and glycidol and their respective esters within fats and oils, especially in edible oils. The present technology provides one or more unique processes of providing fatty acid glyceride streams and triglyceride oils free of organohalo (e.g., 3-chloro-1,2-propandiol), glycidyl or other oxirane species, such as epichlorohydrin, and their respective esters. The processes include both treating oils and/or treating the processing stream used in the making and/or processing of crude or refined oils by the addition of one or more bases. The process includes adding one or more bases to either 1) a triglyceride oil, or 2) to a carboxylic acid ester stream used in the preparation of triglyceride oil. The one or more bases react with a fatty acid or a fatty acid ester within the carboxylic acid stream or triglyceride oil to form a carboxylate anion (soap) and a cation counterion. In some embodiments, additional fatty acid is added with the one or more bases to form the carboxylate anion. The carboxylate anion then reacts with the organohalo or oxirane species to yield an ester and metal halide salt or a metal alkoxide species, respectively. This provides a fatty acid glyceride stream or triglyceride oil with reduced levels of organohalo (e.g., 3-chloro-1,2-propandiol), glycidyl esters or other oxirane species. In some embodiments, the fatty acid glyceride stream or triglyceride oil is essentially free of organohalo, glycidyl esters or other oxirane species.

In one aspect, the present technology provides at least one process of preparing a carboxylic acid ester stream with reduced levels or essentially free of organohalo, glycidyl or other oxirane species. The process comprises adding to the carboxylic acid ester stream an effective amount of a carboxylate anion and a cation counterion to react with the organohalo, glycidyl and oxirane species present in the carboxylic acid ester stream at a temperature of about 80° C. to about 275° C., preferably about 80° C. to about 250° C., more preferably about 140° C. to about 250° C., for a sufficient time to provide a carboxylic acid ester stream with reduced levels or essentially free of organohalo, glycidyl or other oxirane species.

In some aspects, the present technology prevents the formation of organohalo, glycidyl or other oxirane species in a carboxylic acid ester stream or triglyceride oil.

In another aspect, the present technology provides at least one process of removing organohalo, glycidyl or other oxirane species from a triglyceride oil comprising the steps of mixing an effective amount of one or more bases to an effective amount of at least one fatty acid to produce an effective amount of a carboxylate anion and corresponding cation counterion that is sufficient to reduce or remove the organohalo, glycidyl or other oxirane species from the triglyceride oil; mixing the effective amount of the carboxylate anion with the triglyceride oil at a temperature of about 80° C. to about 275° C., preferably about 80° C. to about 250° C., more preferably about 140° C. to about 250° C., for a sufficient time; wherein the oil has reduced levels or essentially free of organohalo, glycidyl or other oxirane species.

In yet a further aspect, the present technology provides a process of reducing, removing, or preventing the formation of organohalo, glycidyl or other oxirane species during processing or a manufacturing procedure for a triglyceride oil comprising the steps of making a triglyceride oil feedstock; adding a sufficient amount of one or more bases to react with a fatty acid within the triglyceride oil feedstock to produce a sufficient amount of a carboxylate anion and a cation counterion to react with the organohalo, glycidyl and other oxirane species present in the feedstock; incubating the feedstock and one or more bases at a temperature of about 80° C. to about 275° C., preferably about 80° C. to about 250° C., more preferably about 140° C. to about 250° C., for a sufficient time to produce a triglyceride oil substantially free of organohalo, glycidyl or other oxirane species. In some aspects, the one or more bases are added at the start of the oil processing or manufacturing procedure. In other aspects, the process further comprises adding a sufficient amount of a fatty acid to react with the one or more bases to produce the carboxylate anion and cation counterion.

In some aspects, the triglyceride oil or carboxylic acid ester stream comprises less than about 0.5 ppm of organohalo, glycidyl or other oxirane species, preferably less than about 0.15 ppm, alternatively less than about 0.1 ppm.

DETAILED DESCRIPTION OF THE INVENTION

The present technology surprisingly provides a method of removing, reducing, eliminating or preventing the formation of organohalo species, glycidyl, or other oxiranes, such as for example, epichlorohydrin, or their respective esters from carboxylic acid esters streams and crude and refined triglyceride oils. The methods provide resultant carboxylic acid ester streams or triglyceride oils that are reduced or, in some embodiments, essentially free of organohalo, glycidyl or other oxirane species.

The term "reduced" organohalo, glycidyl or other oxirane species in relation to the present technology is defined as a reduction by at least 25% or more, preferably at least 40% in the amount of the organohalo, glycidyl or other oxirane species in the carboxylic acid ester streams or crude and refined triglyceride oil when compared to the carboxylic acid ester stream or triglyceride oil not treated with a base as in the present technology. In some embodiments, the amount of the organohalo, glycidyl, or other oxirane species are reduced by at least about 25% or more, at least about 30% or more, alternatively about 35% or more, alternatively about 40% or more, alternatively about 45% or more, alternatively about 50% or more, alternatively about 55% or more, alternatively about 60% or more, alternatively about 70% or more, alternatively about 80% or more, alternatively about 90% or more, and include any percentages there between, including, but not limited to, increments of about 0.1%, about 0.2%, about 0.25%, about 0.3%, about 0.4%, about 0.5%, about 0.6%, about 0.7%, about 0.8%, about 0.9%, about 1% and multiple factors thereof (e.g. about 0.5×, about 1×, about 2.0×, about 2.5×, etc).

The term "essentially free of" organohalo, glycidyl or other oxirane species for the present technology is defined as levels of the organohalo, glycidyl or other oxirane species which are very low levels, for example, less than about 0.5 ppm, more preferably less than about 0.15 ppm, alternatively less than about 0.1 ppm of the compositions of the oil. In some embodiments, "essentially free of" would encompass undetectable levels of these compounds. The amount of organohalo, glycidyl or other oxirane species within the oil can be calculated or estimated by any means known in the art, including gas chromatography (GC) mass spectrometry, liquid chromatography (LC) mass spectrometry and the like. Commercial laboratories that can perform these measurements include, but are not limited to, Eurofins Central Analytical Laboratories, Metairie, La. and SGS Gmbh, Hamburg, Germany.

In some embodiments, the present technology provides a process for treating both refined and unrefined oil and/or treating the processing carboxylic acid ester stream in the making or processing of refined oils to reduce, remove or prevent the formation of the organohalo, glycidyl or other oxirane species from the end-product oil. Not to be bound by any theory, but by information and belief, it is believed that the addition of one or more bases to the carboxylic acid ester stream during manufacturing of a triglyceride oil prevents the formation of one or more organohalo, glycidyl or oxirane species from forming in the end product triglyceride oil.

In some embodiments, the present technology provides a process of treating a carboxylic acid ester stream in the process of making an oil to prevent the formation of organohalo, glycidyl or oxirane species.

Treating Triglyceride Oil During Processing

In some embodiments, the present technology provides a process for producing carboxylic acid ester streams with reduced levels or essentially free of organohalo species (e.g., 3-chloro-1,2-propandiol), glycidol or oxirane species and their respective esters. The process involves chemically modifying the organohalo, glycidyl or oxirane species from the oil so that it can be separated out from the carboxylic acid ester stream, in some instances by filtration. The process includes adding at least one base either during the processing and/or manufacture of a carboxylic acid ester stream or after the carboxylic acid ester stream is produced into a triglyceride oil. The at least one base reacts with a fatty acid or a fatty acid ester within the carboxylate acid stream to form a carboxylate anion (soap) and its cation counterion as depicted below:

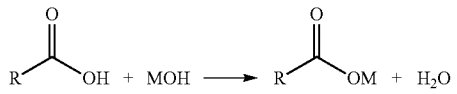

wherein R represents a carbon chain length from $C_1$ to $C_{23}$ and wherein M is an alkali metal, an alkaline earth metal, a transition metal, or a nitrogen- or phosphorous-containing cationic species. The carboxylate anion and cation counterion reacts with the organohalo or glycidyl species to yield an ester and metal halide salt or a metal alkoxide species, respectively as shown below:

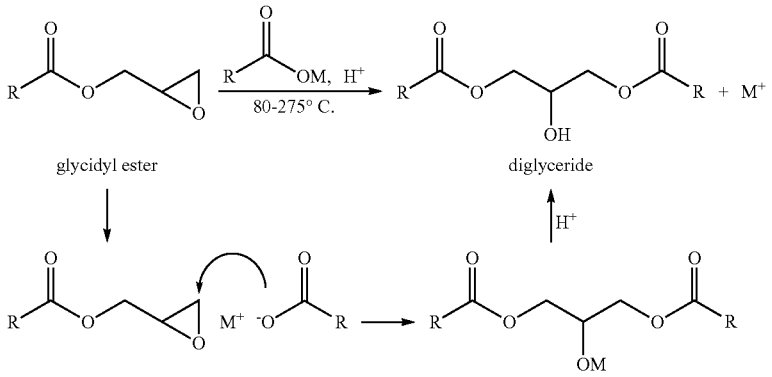

-continued

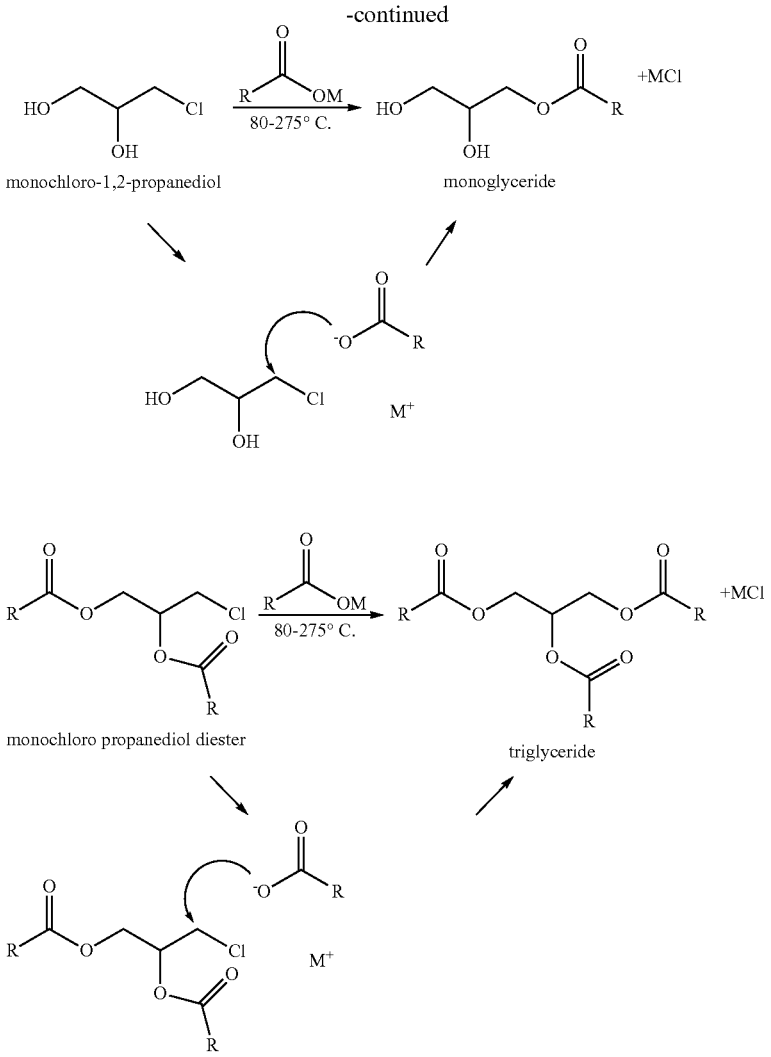

wherein R represents a carbon chain length from $C_2$ to $C_{24}$ and wherein M is an alkali metal, an alkaline earth metal, a transition metal, or a nitrogen- or phosphorous-containing cationic species. In some embodiments, the metal halide salt formed can be filtered out from the refined or processed carboxylic acid stream, providing a filtered carboxylic acid ester stream with reduced levels or essentially free of organohalo (e.g., 3-chloro-1,2-propandiol), glycidol or oxirane species and their respective esters.

In the present technology, carboxylic acid ester streams include, but are not limited to, any compound or components within the stream of manufacturing, refining, processing or purifying fats and oils, including, but not limited to, fats, oils, fatty acids and glycerols and the like. The terms fatty acid and carboxylic acids are interchangeable for use in the present application. Fats and oils include, but are not limited to, any triglyceride oils, including raw and purified oils, vegetable oils, animal fat, and synthetic oils. Fats and oils are composed of triglycerides, esters of glycerol and fatty acids. Natural fats and oils are composed principally of triglycerides, but other components may be present in minor quantities, including, but not limited to, fatty acids, partial glycerides, diglycerides and monoglycerides. Triglycerides are also called triacylglycerols (TAG) and are esters derived from glycerol and three fatty acids. Suitable triglyceride oils include, but are not limited to coconut oil, cochin oil, corn oil, cottonseed oil, linseed oil, olive oil, palm oil, palm kernel oil, peanut oil, soybean oil, sunflower oil, tall oils, tallow, lesquerella oil, tung oil, whale oil, tea seed oil, sesame seed oil, safflower oil, rapeseed oil, fish oils, avocado oil, mustard oil, rice bran oil, almond oil, walnut oil, derivatives thereof, and combinations thereof.

In some embodiments, the processes of manufacturing, refining, processing or purifying fats and oils include any process known to one skilled in the art. These processes include, but are not limited to, physical, steam or mechanical refining (including, but not limited to, for example, vacuum steam distillation), chemical refining (including, but not limited to, for example, solvent extraction and miscella refining), and treatment by bleaching clay, basic or acidic resin, silica, alumina and/or active carbon. In the present technology, organohalo, glycidyl or other oxirane species are removed by the addition of at least one base during the processing steps of the triglyceride oil or carboxylic acid ester stream. The at least one base may be added at the beginning of the processing or manufacturing step, during the processing and manufacturing steps, or after the processing or manufacturing steps of a triglyceride oil. If added during the processing or after the processing of the triglyceride oils, additional fatty acids may also be added to produce sufficient amounts of the carboxylate anion and counter cation, or alternatively already formed carboxylate anion and counter cation may be added.

In the present technology, the at least one base is added in an amount sufficient to remove a sufficient amount of the organohalo, glycidyl or other oxirane species from the triglyceride oil or carboxylic acid stream. A sufficient amount of the at least one base includes an amount able to react with a sufficient amount of fatty acid to produce a sufficient amount of carboxylate anion and cation counterion to react with organohalo, glycidyl or other oxirane species present or formed during the processing or manufacturing to reduce the amount of organohalo, glycidyl or oxirane species or, in some embodiments, produce an oil that is substantially free of organohalo, glycidyl or oxirane species. If the at least one base is added at the beginning or during the processing or manufacturing of the triglyceride oil, the at least one base can be added in excess of the amount of organohalo, glycidyl or other oxirane species anticipated to be formed in the final end-product triglyceride oil. The anticipated amount of organohalo, glycidyl or other oxirane species can be estimated by one skilled in the art familiar with manufacturing and processing techniques, and can also be determined by measuring the amount of organohalo, glycidyl or oxirane species in the untreated oil.

In some embodiments, the amount of based added during processing or manufacturing of the oil is about 100 parts per million (ppm) to about 2% based on total weight of the triglyceride oil, preferably about 200 ppm to about 2% based on total weight of the triglyceride oil. The base can be added in an excess of the organohalo, glycidyl or other oxirane species present or anticipated to be formed, preferably about 1.1 fold to about 10,000 fold excess, preferably about 1.1 fold to about 20 fold excess, preferably about 2 fold to about 10 fold excess. Alternatively, the base can be added in excess of the organohalo, glycidyl or oxirane species present or anticipated in about 1.1 fold to about 1,000 fold excess, alternatively from about 1.1 fold to about 500 fold excess, alternatively from about 1.1 fold to about 250 fold excess, alternatively from about 1.1 fold to about 100 fold excess, alternatively from about 1.1 fold to about 50 fold excess, alternatively from about 1.1 fold to about 25 fold excess, alternatively from about 1.1 fold to about 20 fold excess, alternatively from about 2 fold to about 1000 fold excess, alternatively from about 2 fold to about 500 fold excess, alternatively from about 2 fold to about 250 fold access, alternatively from about 2 fold to about 100 fold excess, alternatively from about 2 fold to about 50 fold excess, alternatively from about 2 fold to about 25 fold excess, and includes any percentage or range there between, including, but not limited to, increments of about 0.1, about 0.2, about 0.3, about 0.4, about 0.5, about 0.6, about 0.7, about 0.8, about 0.9 or about 1.0 fold and multiplied factors thereof (e.g. about 0.5×, about 1.0×, about 2.0×, about 2.5×, about 3.0×, about 4.0×, about 5.0×, about 10×, about 50×, or 100× or greater). In some embodiments, the fold excess can be about 2 fold, about 3 fold, about 4 fold, about 5 fold, about 6 fold, about 7 fold, about 8 fold, about 9 fold, about 10 fold, about 11 fold, about 12 fold, about 13 fold, about 14 fold, about 15 fold, about 16 fold, about 17 fold, about 18 fold, about 19 fold, about 20 fold, about 21 fold, about 22 fold, about 23 fold, about 24 fold, about 25 fold, about 30 fold, about 35 fold, about 40 fold, about 45 fold, about 50 fold, about 55 fold, about 60 fold, about 65 fold, about 70 fold, about 75 fold, about 80 fold, about 85 fold, about 90 fold, about 95 fold, about 100 fold, about 105 fold, about 110 fold, about 115 fold, about 120 fold, about 125 fold, about 130 fold, about 135 fold, about 140 fold, about 145 fold, about 150 fold, about 175 fold, about 200 fold, about 250 fold, about 300 fold, about 350 fold, about 400 fold, about 450 fold, about 500 fold excess of base.

In some embodiments, the one or more bases is added in a sufficient amount to produce at least about 350 ppm or more of the carboxylate anion (soap) or cation counterion within the carboxylic acid ester stream or triglyceride oil, preferably at least about 400 ppm or more, to react with the organohalo, glycidyl or other oxirane species. In some embodiments, a sufficient amount of the carboxylate anion or cation counterion may be directly added to the carboxylic acid ester stream or the unrefined or refined triglyceride oil, wherein the sufficient amount is at least about 350 ppm or more, more preferably about 400 ppm or more. In some embodiments, the amount of the carboxylate anion formed or added includes, but is not limited to, about 350 ppm or more, about 400 ppm or more, about 450 ppm or more, about 500 ppm or more, about 550 ppm or more, about 600 ppm or more, about 650 ppm or more, about 700 ppm or more, about 800 ppm or more, about 900 ppm or more, about 1000 ppm or more, about 1200 ppm or more, about 1500 ppm or more, about 1800 ppm or more, about 2000 ppm or more, about 2500 ppm or more, and includes any ppm amount there between, including, but not limited to, for example, increments of about 0.1 ppm, about 0.25 ppm, about 0.5 ppm, about 1 ppm, about 2 ppm, about 5 ppm, about 10 ppm, about 20 ppm, about 25 ppm, about 50 ppm, about 100 ppm, and multiple factors thereof (e.g. about 0.5×, about 1.0×, about 2×, about 2.5×, about 5×, etc).

The at least one base can be added during any step of the processing and/or manufacturing of the triglyceride oil, including, but not limited to, refining, degumming, deodorizing, washing, bleaching, distillation, refining, and the like and any combination thereof. In some embodiments, depending on what stage of the processing/manufacturing of the oil the one or more bases is added, free fatty acid can also be added in an amount sufficient to react with the one or more bases to produce a sufficient amount of carboxylate anion to reduce or remove the organohalo, glycidyl or other oxirane species from the end-product oil and provide an oil with reduced levels or essentially free of organohalo, glycidyl or other oxirane species. Preferably, a fatty acid naturally found in the oil being manufactured or processed is used.

The reaction of the carboxylate anion (and cation counterion) with the organohalo, glycidyl or other oxirane species occurs at a temperature of about 80° C. to about 275° C., alternatively about 80° C. to about 250° C., preferably about 120° C. to about 275° C., preferably about 140° C. to about 240° C., more preferably about 180° C. to about 230° C., and includes any ranges or temperatures there between, including increments of about 0.1, about 0.2, about 0.3, about 0.4, about 0.5, about 0.6, about 0.7, about 0.8, about 0.9, about 1.0 and multiple factors thereof (e.g. about 0.5×, about 1×, about 2×, about 3×, about 4×, about 5×, about 10×). Suitable temperatures include, but are not limited to, about 80° C., about 90° C., about 100° C., about 110° C., about 120° C., about 130° C., about 140° C., about 150° C., about 160° C., about 170° C., about 180° C., about 190° C., about 200° C., about 210° C., about 220° C., about 230° C., about 240° C., about 250° C., about 260° C., about 270° C., about 275° C. and includes any temperature there between in increments of about 0.1, about 0.2, about 0.25, about 0.3, about 0.4, about 0.5, about 0.6, about 0.7, about 0.8, about 0.9, about 1.0 and multiple factors thereof.

The reaction is maintained for a sufficient time until the triglyceride oil is essentially free of organohalo, glycidyl or other oxirane species. Suitable reaction times include, but are not limited to, about 30 minutes or more, preferably about one hour or more, and include, but are not limited to, for example, about 30 minutes or more, about 45 minutes or more, about 50 minutes or more, about one hour or more, about two hours or more, about three hours or more, about four hours or more, about 5 hours or more, about 6 hours or more, about 7 hours or more and includes any amounts of time there between. Reaction times will depend on both the amount of the carboxylate anion and cation counter ion present in the reaction mixture and the reaction temperature. In general, the reaction time will be longer when a temperature at the lower end of the temperature range is used, and shorter when a temperature at the high end of the temperature range is used. Similarly, reaction times will be longer when amounts of carboxylate anion and cation counterion present in the reaction stream are at the lower end of the range, for example at about 350 ppm to about 400 ppm, and will be shorter when amounts greater than about 400 ppm are present.

In one embodiment, the present technology includes a process of reducing or removing organohalo, glycidyl or other oxirane species from a triglyceride oil comprising the steps of mixing an effective amount of the one or more bases with an effective amount of at least one fatty acid to produce an effective amount of a carboxylate anion and corresponding cation counter ion that is sufficient to reduce or remove the organohalo, glycidyl or other oxirane species from the triglyceride oil; and mixing the effective amount of the carboxylate anion with triglyceride oil at a temperature of about 80° C. to about 275° C., alternatively about 80° C. to about 250° C., preferably 140° C. to about 250° C. In some embodiments, the reacted mixture is then filtered by methods known in the art, for example, but not limited to, filter press or bag filter, to remove the halide salt species formed. The filtered oil has reduced levels or is essentially free of organohalo, glycidyl or other oxirane species.

During the manufacture and processing of a triglyceride oil, free fatty acids are found within these oils which are usually removed during the further processing steps of, for example, physical or chemical refining or deodorization. In the present technology, fatty acids found within the triglyceride oils can be used to react with the added base and/or bases to produce the carboxylate anion (and cation counter ion). Depending on how much free fatty acid is within the triglyceride oil, additional fatty acid can be added to produce a sufficient amount of carboxylate anion (and cation counterion) to react with the organohalo, glycidyl or other oxirane species present or estimated in the triglyceride oil or carboxylic acid ester stream.

Removal of Organohalo, Glycidyl or Other Oxirane Species from Refined Oil or after Processing of the Triglyceride Oil In some embodiments of the present technology, the triglyceride oil is already processed, for example a refined or unrefined fatty acid oil. In this process, a sufficient amount of one or more bases is added (and if necessary, additional amount of at least one fatty acid) to produce a sufficient amount of carboxylate anion (and cation counterion) to react with the amount of organohalo, glycidyl or other oxirane species within the oil. The amount of organohalo, glycidyl or other oxirane species within the oil can be calculated or estimated by any means known in the art, including gas chromatography (GC) mass spectrometry, liquid chromatography (LC) mass spectrometry and the like. In the case of refined oils, the fatty acids have been removed during the refining procedure and thus fatty acids are also added along with the one or more bases. In the case of non-refined oils some free fatty acids may be available to react with the one or more bases, and thus some or no extra fatty acids can be added with the one ore more bases, depending on the type of oil.

In some embodiments, at least one base is reacted with fatty acids (preferably a fatty acid which is natively found within the triglyceride) to create the carboxylate anion. The carboxylate anion is then reacted with the triglyceride oil to reduce or remove organohalo, glycidyl or other oxirane species. The carboxylate anion is added in a sufficient amount to reduce or remove a sufficient amount of the organohalo, glycidyl or other oxirane species to provide a triglyceride oil with reduced levels or essentially free of organohalo, glycidyl or other oxirane species. A sufficient amount of carboxylate anion is, as described above, at least about 350 ppm, alternatively at least about 400 ppm or more. This reaction is carried out as described above, at a temperature of about 80° C. to about 275° C., alternatively about 80° C. to about 250° C., preferably about 120° C. to about 275° C. A sufficient amount of time is, as described above, greater than about 30 minutes, alternatively an hour or more, alternatively two hours or more.

The carboxylate anion can be reacted with the triglyceride oil in different ways. For example, the carboxylate anion can be generated in or added to the reactor in which the triglyceride oil was formed (single pot method). Alternatively, the triglyceride oil can be added to a second reactor or a series of reactors, and the carboxylate anion can be added to the second reactor or the series of reactors (sequential method). In a further embodiment, triglyceride oil streams can flow over a reactor bed containing the carboxylate anion and cation counterion.

Carboxylate anions and their cation counterion of the present technology include metal carboxylates of the following structure:

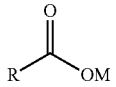

wherein R is $C_2$ to $C_{24}$ and M is an alkali metal, an alkaline earth metal, a transition metal, or a nitrogen- or phosphorous-containing cationic species. Any suitable alkali metal, alkaline earth metal or transition metal may be used, including, but not limited to, for example, iron, copper, calcium, magnesium, aluminum, potassium, sodium, and the like. In some preferred embodiments, the metals that can be used in edible oils are preferably those that are found naturally in the body, including, but not limited to, calcium, magnesium, copper, potassium, sodium, and the like. The metal can be chosen based on a number of factors, including, but not limited to, cost and final application. Suitable final applications include, but are not limited to, for example, edible foods, pet food, cosmetics, flavor carriers, pharmaceuticals and the like.

The oils or carboxylic acid ester streams of the present technology are filtered using standard filtering techniques known in the art. In some embodiments, the oils are filtered using standard filtration equipment, including, but not limited to, for example, a bag filter, cartridge filter or plate and frame filter press. Typical filter pore sizes for these filters include pore sizes in the range of about 0.5 microns to about 100 microns. If necessary, a filtering aid such as diatomaceous earth or kieselguhr could be used to improve the filtration process.

Processes other than filtration can also be used to remove the resulting metal halide salt or metal alkoxide species from the oils or carboxylic acid ester streams. Such other processes that can be used include, but are not limited to, washing, centrifuging, winterization, extraction, acidification with a mineral acid, settling and miscella refining.

Any suitable fatty acids (carboxylic acids) may be used in the processing of making carboxylic acid ester streams, including, but not limited to, fatty acids derived from animal and vegetable sources, any feedstocks known in the art, including, but are not limited to, an alkyl ester of a carboxylic acid, carboxylic anhydride or carboxylic derivatives such as halides (acyl halides), carbonates, other carboxylate species, (e.g., mixed anhydrides) or heteroatom derivatives, such as, for example imidazolides, ortho esters, silyl esters, hydrazines.

In the present technology, any suitable base can be used that can react with the fatty acid to produce a carboxylate anion. Suitable bases include, but are not limited to, for example, carbonate, bicarbonate, hydroxide, oxide, alkoxide, amine bases, hydrides, phosphines and the like. In some embodiments, the one ore more bases are added in excess of the amount of organohalo, glycidyl or other oxirane species in the carboxylic acid ester stream or triglyceride oil.

In one embodiment, the present technology provides a method of removing organohalo, glycidyl or other oxirane species from short and medium chain triglycerides (for example, short chain fatty acids have from 2-5 carbons and medium chain triglycerides have from 6-10 carbons) by deodorizing the triglyceride oil after addition of the carboxylate anion and cation counterion and described above. The process of deodorization includes the standard deodorization steps known in the art, for example, such steps can include heating the mixture for about 20 to about 30 minutes at a temperature of about 180° C. to about 200° C. under vacuum of about 2 mmHg to about 15 mmHg, and running steam through the mixture to remove impurities. While deodorization steps can be used to remove some of the organohalo, glycidyl or other oxirane species from short and medium chain triglycerides, deodorization alone, without the addition of carboxylate anion and cation counterion, is not sufficient to substantially reduce the amount of these impurities present in the triglyceride oils. Moreover, deodorization of heavier triglycerides such as $C_{12}$ chains and higher, can actually cause the formation of organohalo, glycidyl or other oxirane species in these heavier triglyceride oils.

The present technology may be used for the reduction or removal of organohalo, glycidyl, or oxirane species from any triglyceride oils known in the art, including, but not limited to, edible and food grade oils and their analogs (monoglycerides and diglycerides), lubricating oils, synthetic oils, specialty polymers and personal care applications, and pharmaceuticals.

The presently described technology and its advantages will be better understood by reference to the following examples. These examples are provided to describe specific embodiments of the present technology. By providing these specific examples, it is not intended limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Example 1

Removal of 3-chloro-1,2-propanediol diesters from Capric/Caprylate Acids

Extra MCPD was added to a triglyceride reaction stream to determine if the base could remove the MCPD from the triglyceride oil. Glycerol (23.62 g, 0.256 mol), capric/caprylic fatty acids (129.1 g, 0.822 mol), preformed capric/caprylic fatty acid esters of 3-chloro-1,2-propanediol and C8/C10 fatty acids (3.05 g, 0.0078 mol) and potassium carbonate (base, 2.03 g, 0.0147 mol) were combined. The reaction was mixed and heated to about 210° C. over 11.5 hours. After holding at about 150° C. for 1 hour, the reaction solution was heated to about 210° C. over one hour and then held at about 210° C. for 3 hours. The solution was filtered using 50 micron filter paper. After the second hold period, no organochloro species were detected by GC.

Example 1 illustrates that a base can be added during the manufacture of a triglyceride oil to effectively remove MCPD impurities from the resulting triglyceride oil.

Example 2

Removal of 3-chloro-1,2-propandiol in a Glyceride Reaction System

This example illustrates that the addition of a base to a triglyceride reaction stream is effective to remove MCPD impurities during manufacture of the triglyceride oil. Caprylate/capric fatty acids (52% caprylate, 640.45, 4.08 mol), glycerol, (108.7 g, 1.18 mol) and potassium carbonate (base) were combined. The mix was held for 20 minutes. After the offgassing has stopped, carbon (3.54 g) and 3-chloro-1,2-propanediol (2.79 g, 0.0244 mol) were added to the reaction mixture. The mix was heated to about 235° C. over 2 hours and held at about 235° C. for four additional hours. Upon cooling, the mix was filtered and unreacted fatty acids were converted to methyl esters (vial methanol and sulfuric acid). Upon analysis of the triglyceride oil by an outside laboratory, Eurofins Central Analytical Laboratories, Metairie, La., the total 3-MCPD (free and bound) was found by GC mass spectrometry to be less than 0.15 mg/kg of total composition.

Example 3

Removal of 3-MCPDs During Triglyceride Formation

This example illustrates that the addition of a base to a reaction stream containing an alkyl ester feedstock is effective to remove or prevent the formation of MCPD impurities during the manufacture of the triglyceride oil. Methyl esters of C8/C10 fatty acids (500 g) and potassium carbonate (1.7 g) were combined and heated to about 175° C. Glycerol (78.6 g) was then added to the reaction mixture and the mixture was heated to about 235° C. and held at about 235° C. for 3 hours. Excess methyl esters were removed in vacuo and the resultant triglyceride was filtered under vacuum using 50 micron paper. Analysis by the outside lab, Eurofins Central Analytical Laboratories, Metairie, La., showed the level of total 3-MCPD (free and bound) to be less than about 0.15 mg/kg using GC mass spectrometry.

Example 4

Removal of Glycidyl Esters from a Pre-Formed Triglyceride

This example illustrates that a base (and additional fatty acids) can be added to a triglyceride oil product to effectively remove glycidyl ester impurities. A deodorized caprylate/capric triglyceride (99.95 g), C8/C10 fatty acids (3.3 g) and potassium carbonate (0.45 g) were combined and heated to about 200° C. At about 200° C., glycidyl butyrate (1.54 g) was added. The mixture was incubated at about 200° C. for 1 hour, and the sample was filtered and analyzed for glycidyl content. No glycidyl species were detectable by gas chromatography.

Example 5

Removal of Organochloro and Oxirane Species in a Glyceride Reaction System at Reaction Temperature This example illustrates that the addition of a base to a triglyceride reaction stream is effective at triglyceride reaction temperatures to remove or prevent the formation of MCPD impurities during the manufacture of the triglyceride oil. C8/C10 fatty acids (647.69 g, 4.125 mol), sodium carbonate (2.00 g, 0.0189 mol) and carbon (3.48 g) were combined and heated to about 210° C. Glycerol (108.85 g, 1.182 mol) was added over four hours. The mix was heated to about 245° C. and held for 6 hours. The soap concentration was about 8,960 ppm. The carbon was removed via filtration. Upon analysis by an outside laboratory, the total 3-MCPD (free and bound) was found to be less than 0.15 mg/kg as determined by GC mass spectrometry.

Example 6

Removal of Chloro and Oxirane Species in a Glyceride Reaction System at Reaction Temperature In this example, a run similar to Example 5 was conducted using similar reactants and similar reaction conditions, except that potassium carbonate was used as the base and the soap concentration was about 1,180 ppm. Upon analysis by an outside laboratory, the total 3-MCPD (free and bound) was found to be less than 0.15 mg/kg as determined by GC mass spectrometry.

This example illustrates that, in comparison to Example 5, a lower soap concentration can be used which is still effective to remove or prevent the formation of MCPD impurities.

Example 7

Removal of Chloro and Oxirane Species in a Glyceride Reaction System at Reaction Temperature In this example, a run similar to Example 5 was conducted using similar reactants and similar reaction conditions, except that the soap concentration was about 660 ppm. Upon analysis by an outside laboratory, the total 3-MCPD (free and bound) was found to be 0.23 mg/kg as measured by GC mass spectrometry. Untreated medium chain triglycerides (MCTs) from this manufacturing process typically have MCPD levels of greater than 0.5 ppm as measured by GC mass spectrometry.

This example illustrates that, although the soap concentration of 660 ppm was not effective under the particular time and temperature conditions employed in this example to reduce the MCPD levels to non-detectable levels, it was still effective to reduce the MCPD impurities by about 50% compared to typical levels found in a similar untreated triglyceride. It is expected that at the soap concentration of 660 ppm, increasing the reaction temperature or reaction time or both would have resulted in a total MCPD concentration of less than 0.15 mg/kg.

Example 8

Treatment of a crude oil stream at 200° C.

An unrefined triglyceride of $C_8$-$C_{10}$ fatty acids (612.56 g) was obtained from a typical Production run (48,000 lb crude product). To this material potassium carbonate (0.76 g, 0.12 wt %) was added. The resulting soap concentration was about 3,500 ppm. The reaction mix was heated to about 200° C. over 2 hours and then held at about 200° C. for an additional 2 hours. Upon cooling the mix was filtered. The MCPD levels in the unrefined triglyceride before and after treatment with the base were measured by GC mass spectrometry by an outside laboratory, SGS Gmbh Hamburg, Germany. After treatment, the MCPD level in the filtered stream was reduced to below detectable limits (<0.10 mg/kg) compared to a starting MCPD concentration of 0.57 mg/kg.

Example 9

Treatment of a Crude Oil Stream at 170° C.

An unrefined triglyceride of C8-C10 fatty acids (604.97 g) was obtained from a typical Production run (48,000 lb crude product). To this material potassium carbonate (0.85 g, 0.14 wt %) was added. The resulting soap concentration was about 3,970 ppm. The reaction mix was heated to about 170° C. over 2 hours and then was held at about 170° C. for an additional 2 hours. Upon cooling the mix was filtered. The MCPD levels in the unrefined triglyceride before and after treatment with the base were measured by GC mass spectrometry by an outside laboratory, SGS Gmbh Hamburg, Germany. After treatment, the MCPD level in the filtered stream was reduced to 0.33 mg/kg as compared to a starting MCPD concentration of about 0.57 mg/kg.

Examples 8 and 9 illustrate the relationship between reaction time, reaction temperature, and soap concentration in removing the organochloro and oxirane species. The reaction temperature of Example 9 was lower than Example 8 (170° C. compared to 200° C.) and the soap concentration was slightly higher (3,970 ppm compared to 3,500 ppm), while the reaction times were the same. The conditions of time, temperature and soap concentration employed in Example 8 were sufficient to remove the MCPD impurities to below the detectable limits, whereas the conditions employed in Example 9 were sufficient to remove some of the MCPD impurities (about a 40% reduction). It is expected that the MCPD concentration would have been below detectable limits (less than 0.10 mg/kg) in Example 9 if a higher concentration of soap had been used, keeping the reaction temperature and reaction time of Example 9 the same. Alternatively, a higher reaction temperature or longer reaction time, or both, could have been used in Example 9 to remove more of the MCPD impurities at the given soap concentration.

The presently described technology is now described in such full, clear, concise and exact terms as to enable any person skilled in the art to which it pertains, to practice the same. It is to be understood that the foregoing describes preferred embodiments of the technology and that modifications may be made therein without departing from the spirit or scope of the invention as set forth in the appended claims.

In the present specification, use of the singular includes the plural except where specifically indicated.

The invention claimed is:

1. A process of preparing a carboxylic acid ester stream with reduced levels of organohalo, glycidyl or other oxirane species, the process comprising: adding to the carboxylic acid ester stream an effective amount of a carboxylate anion to react with all of the organohalo, glycidyl and oxirane species present in the carboxylate acid ester stream at a temperature of [80° C. to 275° C.] *140° C. to 250° C.*, wherein the carboxylate anion reacts with the organohalo, glycidyl or oxirane species for a sufficient amount of time to provide a carboxylic acid ester stream with reduced levels of organohalo, glycidyl or other oxirane species.

2. A process of removing organohalo, glycidyl or other oxirane species from a triglyceride oil comprising the steps of: mixing an effective amount of at least one base to an effective amount of at least one fatty acid to produce an effective amount of at least one carboxylate anion and corresponding cation counterion that is sufficient to remove the organohalo, glycidyl or other oxirane species from the triglyceride oil; mixing the effective amount of the carboxylate anion with the triglyceride oil at a temperature of about [80° C. to about 275° C.] *140° C. to about 250° C.*, wherein the carboxylate anion reacts with the organohalo, glycidyl or oxirane species for a sufficient amount of time to provide a triglyceride oil product with reduced levels of organohalo, glycidyl or other oxirane species.

3. A process of removing or preventing the formation of organohalo, glycidyl or other oxirane species during a processing or a manufacturing procedure for a triglyceride oil comprising the steps of: making a triglyceride oil feedstock; adding a sufficient amount of at least one base to react with a sufficient amount of fatty acid within the triglyceride oil feedstock to produce a carboxylate anion and a cation counter ion in an amount sufficient to react with the organohalo, glycidyl and oxirane species present in the feedstock; incubating the feedstock containing the at least one base at a temperature of about [80° C. to about 275° C.] *140° C. to about 250° C.* for a sufficient amount of time to produce a triglyceride oil with reduced levels of organohalo, glycidyl or other oxirane species.

4. The process of claim 1, wherein the carboxylate anion is added at the start of the oil processing or manufacturing procedure.

5. The process of claim 3, wherein the process further comprises adding a sufficient amount of at least one fatty acid to react with the at least one base to produce the carboxylate anion and cation counter ion.

6. The process of claim 1, wherein the carboxylate anion is added after one or more of the processing steps, wherein the processing steps comprise refining, degumming, deodorization, washing, bleaching, distillation, or any combination thereof.

7. The process of claim 3, wherein the carboxylate anion is added after the steps of processing to a purified triglyceride oil.

8. The process of claim 3, wherein the triglyceride oil is a C2 to C24 chain triglyceride.

9. The process of claim 8, wherein the triglyceride oil is a C2 to a C18 chain triglyceride.

10. The process of claim 8, wherein the triglyceride oil is an edible oil.

11. The process of claim 10, wherein any residual organohalo, glycidyl or other oxirane species in the edible oil is removed by a further step of:

deodorizing the triglyceride oil.

12. The process of claim 3, wherein the cation counterion of the carboxylate anion is an alkali metal, an alkaline earth metal, a transition metal, a nitrogen- or phosphorous-containing cationic species, or combinations thereof.

13. The process of claim 3, wherein the carboxylate anion and cation counter ion is of the formula:

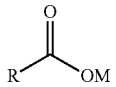

wherein R is a C2 through C24 carbon and M is an alkali metal, an alkaline earth metal, a transition metal, or a nitrogen- or phosphorous-containing cationic species.

14. The process of claim 3, wherein the at least one base is added in excess of the amount of the organohalo, glycidol or oxirane (ethylene oxide) species within the triglyceride oil.

15. The process of claim 14, wherein the base is provided in about 1.1 to about 10,000 fold molar excess of the amount of organohalo, glycidyl or other oxirane species in the triglyceride oil.

16. The process of claim 14, wherein the base is provided in an amount sufficient to produce at least 350 ppm or more of the carboxylate anion.

17. The process of claim 3, wherein the processed triglyceride oil comprises less than about 0.5 ppm of organohalo, glycidyl or other oxirane species.

18. The process of claim 17, wherein the triglyceride oil comprises less than about 0.15 ppm of organohalo, glycidyl or other oxirane species.

[19. The process of claim 18, wherein the preferred temperature range is about 120° C. to about 250° C.]

20. The process of claim [19] *17*, wherein the preferred temperature range is from about 180° C. to about 230° C.

21. The process of claim 3, wherein the carboxylate anion is added in excess of the amount of the organohalo, glycidol or oxirane (ethylene oxide) species within the triglyceride oil.

22. The process of claim 21, wherein the carboxylate anion is provided in an amount of at least 350 ppm or greater.

23. The process of claim 1, wherein the processed carboxylic acid ester stream comprises less than about 0.5 ppm of organohalo, glycidyl or other oxirane species.

24. The process of claim 23, wherein the carboxylic acid ester stream comprises less than about 0.15 ppm of organohalo, glycidyl or other oxirane species.

25. The process of claim 1, wherein a metal halide salt or metal alkoxide species resulting from the reaction are removed by an additional processing step.

26. The process of claim of 25, wherein the additional processing step is selected from the group consisting of filtration, washing, centrifuging, winterization, extraction, acidification with a mineral acid, settling, and miscella refining.

27. The process of claim 1, wherein a sufficient amount of time is greater than 30 minutes.

28. The process of claim 27, wherein a sufficient amount of time is one hour or greater.

29. The process of claim 2, wherein the triglyceride oil product is essentially free of organohalo, glycidyl or oxirane species.

30. The triglyceride oil product with reduced levels of organohalo, glycidyl or oxirane species produced by the process of claim 2, wherein reduced levels of organohalo, glycidyl or oxirane species are in comparison to an oil product that does not undergo reaction with an carboxylate anion.

31. The triglyceride oil product of claim 30, wherein the oil product is essentially free of organohalo, glycidyl or oxirane species.

32. The triglyceride oil product of claim 30, wherein the triglyceride oil product comprises less than about 0.5 ppm of organohalo, glycidyl or other oxirane species.

33. The triglyceride oil product of claim 30, wherein the triglyceride oil product comprises less than about 0.15 ppm of organohalo, glycidyl or other oxirane species.

34. The triglyceride oil product of claim 33, wherein the oil product is an edible oil, a synthetic oil, a vegetable oil or an animal fat oil.

35. The process of claim 1, wherein the carboxylic acid ester stream comprises a carboxylic acid, an alkyl ester of a carboxylic acid, carboxylic anhydride, carboxylic derivatives, acyl halides, carbonates, anhydrides, heteroatom derivatives or combinations thereof.

36. The process of claim 3, wherein the triglyceride oil feedstock comprises a carboxylic acid, an alkyl ester of a carboxylic acid, carboxylic anhydride, carboxylic derivatives, acyl halides, carbonates, anhydrides, heteroatom derivatives or combinations thereof.

37. The process of claim 2, wherein the triglyceride oil is selected from the group consisting of coconut oil, cochin oil, corn oil, cottonseed oil, linseed oil, olive oil, palm oil, palm kernel oil, peanut oil, soybean oil, sunflower oil, tall oils, tallow, lesquerella oil, tung oil, tea seed oil, whale oil, sesame seed oil, safflower oil, rapeseed oil, fish oils, avocado oil, mustard oil, rice bran oil, almond oil, walnut oil, derivatives thereof and combinations thereof.

* * * * *